United States Patent [19]

Schmierer et al.

[11] Patent Number: 4,764,624
[45] Date of Patent: Aug. 16, 1988

[54] 1,2,5-SUBSTITUTED IMIDAZOLE COMPOUNDS AND THEIR USE AS GROWTH REGULATORS

[75] Inventors: Roland Schmierer, Todtenweis; Hilmar Mildenberger, Kelkheim; Reinhard Handte, Gablingen; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 919,881

[22] Filed: Oct. 16, 1986

[30] Foreign Application Priority Data

Oct. 19, 1985 [DE] Fed. Rep. of Germany ....... 3537290

[51] Int. Cl.$^4$ .................. A01N 43/50; C07D 233/90
[52] U.S. Cl. ..................................... 71/92; 548/321
[58] Field of Search ............................ 548/321; 71/92

[56] References Cited

U.S. PATENT DOCUMENTS 2,541,924  2/1951  Jones .................... 548/321

Primary Examiner—Richard A. Schwartz
Attorney, Agent, or Firm—Curtis, Morris & Safford

[57] ABSTRACT

The compounds of the formula I

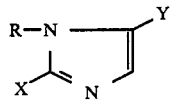

wherein
R denotes (substituted) phenyl, (substituted) cyclohexyl or (substituted) cyclohexenyl,
X denotes a radical of the formulae

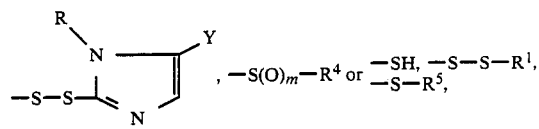

Y denotes a radical of the formulae

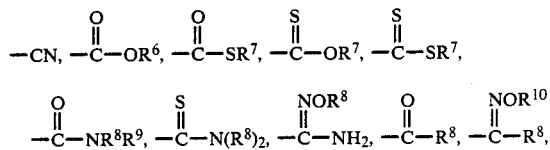

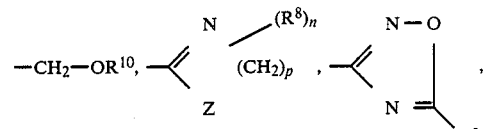

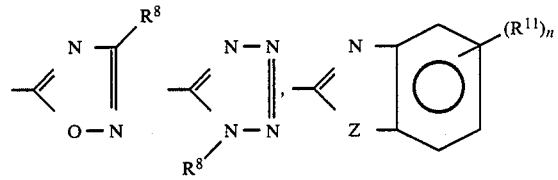

and the bisulfite adducts, acetals, ketals, thioacetals or thioketals derived from

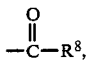

Z denotes O, S or N—$R^8$, m denotes 0, 1 or 2, n denotes 0, 1, 2, 3, or 4 and p denotes 2 or 3, and their salts and quaternization products which are acceptable for agricultural purposes possess advantageous plant growth-regulating actions.

8 Claims, No Drawings

1,2,5-SUBSTITUTED IMIDAZOLE COMPOUNDS AND THEIR USE AS GROWTH REGULATORS

It is known that 1-phenylimidazole-5-carboxylic acid derivatives (cf. DE-A No. 32 17 094) possess plant growth-regulating properties. Surprisingly, it has now been found that compounds substituted in the 2-position of the imidazole ring by sulfur derivatives possess advantageous plant growth-regulating actions in various crops.

The present invention therefore relates to the novel compounds of the formula I

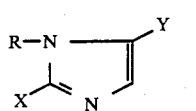
(I)

wherein
R denotes the radical of the formulae

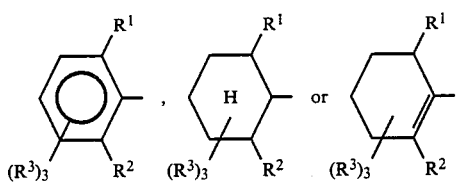

X denotes a radical of the formulae

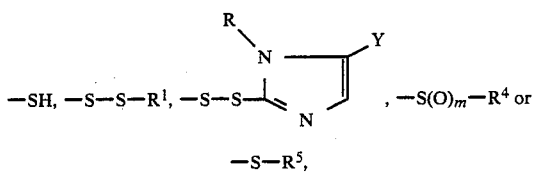

Y denotes a radical of the formulae

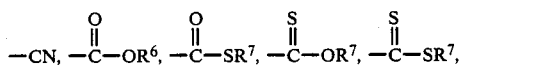

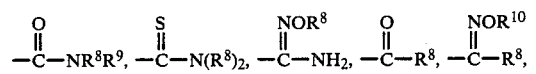

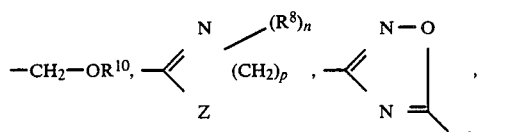

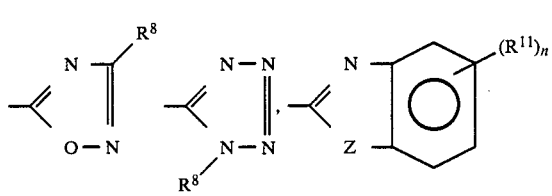

and the bisulfite adducts, acetals, ketals, thioacetals or thioketals derived from —CO—$R^8$
Z denotes O, S or N—$R^8$,
m denotes 0, 1 or 2,
n denotes 0, 1, 2, 3 or 4,
p denotes 2 or 3
$R^1$ and $R^2$ independently of one another denote ($C_1$–$C_4$)-alkyl,
the radicals $R^3$ independently of one another denote hydrogen, ($C_1$–$C_4$)-alkyl, ($C_1$–$C_4$)-alkoxy or halogen,
$R^4$ denotes ($C_1$–$C_4$)-alkyl, ($C_2$–$C_4$)-alkenyl, propargyl, ($C_1$–$C_4$)-alkoxy-carbonyl-($C_1$ or $C_2$)-alkyl, phenyl or benzyl,
$R^5$ denotes ($C_1$–$C_4$)-alkylcarbonyl, benzoyl, N-($C_1$–$C_4$)-alkylcarbamoyl, ($C_1$–$C_4$)-alkoxycarbonyl, phenoxycarbonyl, ($C_1$–$C_4$)-alkoxyoxalyl or, where $R^6$ does not represent a radical of the formula

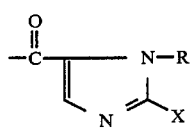

a cation which can be used for agriculture,
$R^6$ denotes hydrogen, ($C_1$–$C_{12}$)-alkyl or ($C_1$–$C_{12}$)-alkyl which is monosubstituted to trisubstituted by hydroxy, halogen, ($C_1$–$C_6$)-alkoxy, ($C_1$–$C_4$)-alkoxy-($C_1$–$C_4$)-alkoxy, ($C_1$–$C_4$)-alkylthio, ($C_1$–$C_4$)-alkylsulfinyl, ($C_1$–$C_4$)-alkylsulfonyl, mono- or di-($C_1$–$C_4$)-alkylamino, cyano, aminocarbonyl, ($C_1$–$C_4$)-alkanoyl, ($C_1$–$C_4$)-alkoxycarbonyl, cyclo-($C_3$–$C_7$)-alkyl, tri-($C_1$–$C_4$-alkyl)-silyl, benzyloxy, benzyloxyethoxy, phenyl or phenyl which is monosubstituted or polysubstituted by halogen or ($C_1$–$C_4$)-alkyl, or by phenoxy or phenylthio, both of which can be monosubstituted or polysubstituted by halogen or ($C_1$–$C_4$)-alkyl, or by oxiranyl, tetrahydrofuryl, triazolyl, pyridyl, imidazolyl, carboxyl, or carboxylate having a cation which can be used for agriculture, or by the radical —O—N═C($CH_3$)$_2$, or denotes ($C_3$–$C_6$)-alkenyl, halogenated ($C_3$–$C_6$)-alkenyl, cyclo-($C_3$–$C_7$)-alkyl which is unsubstituted or substituted by halogen or ($C_1$–$C_4$)-alkyl, cyclo-($C_5$–$C_7$)-alkenyl which is unsubstituted or substituted by halogen or ($C_1$–$C_4$)-alkyl, or denotes ($C_3$–$C_6$)-alkinyl, 1,2-epoxy prop-3-yl, phenyl or phenyl which is monosubstituted or disubstituted by halogen, nitro, cyano, ($C_1$–$C_4$)-alkyl, ($C_1$–$C_4$)-alkoxycarbonyl or ($C_1$–$C_4$)-alkoxy, or denotes ($C_1$–$C_4$)-alkycarbonyl, phenylcarbonyl, where the phenyl ring may be substituted by halogen, nitro, cyano or ($C_1$–$C_4$)-alkyl, a radical of the formulae —N═C($R^{12}$)$_2$, —N$R^8R^{13}$,

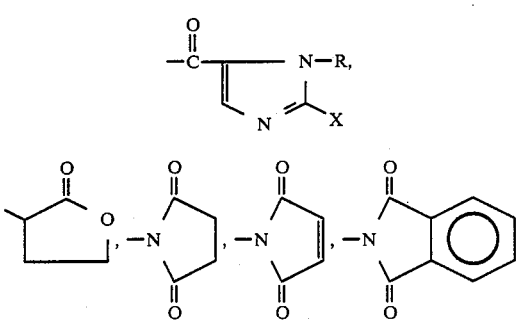

or a cation which can be used for agriculture,
$R^7$ denotes H, ($C_1$–$C_{12}$)-alkyl or ($C_1$–$C_{12}$)-alkyl which is monosubstituted or disubstituted by ($C_1$–$C_4$)- alkoxyethoxy, cyclo-$(C_3-C_6)$-alkyl, benzyloxy, phenyl, phenoxy, $(C_1-C_4)$-alkylthio, $(C_1-C_4)$-alkoxycarbonyl, carboxyl or carboxylate having a cation which can be used for agriculture, or denotes phenyl or, in the case of —CS—$OR^7$, a cation which can be used for agriculture, the radicals $R^8$ in each case independently of one another denote hydrogen, $(C_1-C_6)$-alkyl, phenyl, benzyl or methylphenyl, $R^9$ denotes hydrogen, $(C_1-C_{12})$-alkyl or $(C_1-C_{12})$-alkyl which is monosubstituted or disubstituted by $(C_1-C_6)$-alkoxy, $(C_1-C_4)$-alkoxyethoxy, hydroxyl, halogen, cyclo-$(C_3-C_6)$-alkyl, benzyloxy, cyano, aminocarbonyl, carboxyl, $(C_1-C_4)$-alkoxycarbonyl, formyl, phenyl or phenoxy, phenyl or phenyl which is monosubstituted or disubstituted by halogen, nitro, cyano, $(C_1-C_4)$-alkyl or $(C_1-C_4)$-alkoxy, $(C_3-C_6)$-alkenyl, $(C_3-C_6)$-cycloalkyl, or the radical formulae —$NR^8R^{14}$, —$OR^8$, —NH—CO—$NH_2$, —NH—CS—$NH_2$ or —$SO_2R^8$, or $R^8$ and $R^9$ together with the nitrogen atom to which they are bonded denote a saturated or unsaturated optionally benzofused three-membered to seven-membered ring which contains up to three heteroatoms from the group comprising O, N and S and is unsubstituted or substituted by $(C_1-C_4)$-alkyl or halogen and can contain a carbonyl group, the radicals $R^{10}$ in each case independently of one another denote H or $(C_1-C_{12})$-alkyl which is unsubstituted or substituted by phenyl, halogenophenyl, nitrophenyl, cyanophenyl, $(C_1-C_4)$-alkylphenyl or $(C_1-C_4)$-alkoxyphenyl, hydroxyl, cyano, $(C_1-C_4)$-alkoxycarbonyl, $(C_1-C_4)$-alkylthio, $(C_1-C_4)$-alkoxy, cyclo-$(C_5-C_7)$-alkyl or benzoyloxy, or denote cyclo-$(C_5-C_8)$-alkyl, $(C_3-C_6)$-alkenyl, halogeno-$(C_3-C_6)$-alkenyl, $(C_3-C_6)$-alkinyl, cyclo-$(C_5-C_6)$-alkenyl, $(C_1-C_6)$-alkylcarbonyl, halogeno-$(C_1-C_6)$-alkylcarbonyl having 1 to 3 halogen atoms, $(C_1-C_6)$-alkylaminocarbonyl, benzoyl, halogenobenzoyl or methylbenzoyl, the radicals $R^{11}$ in each case independently of one another denote H, halogen, $(C_1-C_4)$-alkyl, nitro or cyano, the radicals $R^{12}$ independently of one another denote $(C_1-C_6)$-alkyl, cyclo-$(C_3-C_6)$-alkyl, $(C_3-C_6)$-alkenyl, phenyl or benzyl, or the two radicals $R^{12}$ together with the carbon atoms to which they are bonded denote a cyclo-$(C_5-C_7)$-alkyl radical which is unsubstituted or substituted by methyl or halogen, $R^{13}$ denotes $(C_1-C_4)$-alkyl, phenyl, $(C_1-C_6)$-alkylcarbonyl, benzyl, benzoyl, halogenobenzoyl, halogenobenzoyl or methylbenzoyl and $R^{14}$ denotes H, $(C_1-C_4)$-alkyl, formyl, $(C_1-C_6)$-alkylcarbonyl, benzoyl, halogenobenzoyl, methylbenozyl or trihalogenoacetyl, and their salts and quaternization products which are acceptable for agricultural purposes.

Salt formation or quaternization is carried out by addition of suitable compounds at the —S—$R^4$ group or at the basic nitrogen atom of the imidazole ring. Salt formation or quaternization is not possible if $R^5$, $R^6$ or $R^7$ denotes a cation, X represents —SH or $R^6$ or $R^7$ contains a carboxylate group.

Where further basic nitrogen atoms occur in the substituted listed—in addition to the imidazole ring—multiple salt formation or quaternization is also possible.

All inorganic or organic acids which, on the basis of their pK value, are capable of salt formation, for example hydrohalic acid, nitric acid, sulfuric acid, phosphoric acid, phosphonic acid, sulfonic acids, halogenoacetic acids or oxalic acid, are suitable for salt formation at the nitrogen.

Sulfonium salts (salt formation at the sulfur) or quaternization products (salt formation at the nitrogen) are understood as being the reaction products with alkyl halides, alkylthioalkyl halides, alkoxyalkyl halides, in particular $(C_1-C_6)$-alkyl halides and in particular halogenated phenacyl halides which are optionally substituted in the phenyl radical. The salts and quaternization products of the compounds of the formula I are prepared by generally customary methods.

Particularly suitable acetals, ketals and thioketals are those of the formula —$C(OR^{15})_2R^8$ or —$C(SR^{15})_2R^8$, wherein $R^{15}$ denotes $(C_1ORC_2)$-alkyl or the two radicals $R^{15}$ together denote a $C_2$- or $C_3$-alkyl chain which can be substituted by $(C_1-C_4)$-alkyl, monohydroxy-$(C_1-C_4)$-alkyl, halogeno-$(C_1-C_4)$-alkyl having 1 to 3 halogen atoms or phenyl.

Particularly suitable heterocyclic rings for —$NR^8R^9$ are piperidine, morpholine, 2,6-dimethylmorpholine, piperazine, imidazole, thiazole and benzimidazole. The invention embraces all optical isomers of the compounds of the formula I. These can occur when they contain asymmetrically substituted cycloalkyl or cycloalkenyl rings. The alkyl, alkenyl and alkinyl radicals occurring in the definition of the general formula (I) may be either straight-chain or branched.

Halogen is understood as meaning F, Cl, Br or I, in particular F, Cl or Br.

Halogenated $(C_3-C_6)$-alkenyl contains, in particular, 1 to 3 chlorine or fluorine atoms. Halogenophenyl, halogenobenzyl and halogenobenzoyl contain, in particular, 1 to 3 fluorine, chlorine or bromine atoms. Trihalogenoacetyl is understood as meaning, in particular, trichloroacetyl and trifluoroacetyl.

Suitable cations for $R^5$, $R^6$ or $R^7$ which can be used for agriculture are metal cations, for example alkali metal or alkaline earth metal cations, such as Na, K or Mg, or organic cations, such as ammonium containing organic subsituents, or phosphonium, sulfonium, sulfoxonium containing organic substituents, or other nitrogen cations.

Ammonium containing orgaic substituents denotes primary, secondary, tertiary, quaternary, aliphatic, aromatic or heteroaromatic ammonium which can contain 1 to three N atoms. The nitrogen atoms of the amine may also form part of a cyclic system in this case.

The following may be mentioned as examples of such ammonium salts: mono-, di-, tri- and tetra-$[(C_1-C_6)$alkyl]-ammonium, such as isopropylammonium, butylammonium, stearylammonium or triethylammonium, mono-, di- and tri$[(C_1-C_4)$-alkoxy-$(C_1-C_4)$-alkyl]-ammonium or mono-, di- and tri-$[(C_1-C_6)$-alkanol]-ammonium, such as methoxyethylammonium, methoxypropylammonium, triethanolammonium or tripropanolammonium, or ammonium compounds possessing mixed radicals, such as tert-butyldiethanolammonium, triethylbenzylammonium, hydroxyethyltrimethylammonium or chloroethyltrimethylammonium; or allylammonium, diallylammonium, cyclohexylammonium, menthylammonium, aminoethylammonium, ethylenediammonium, benzhydrylammonium, pyrrolidinium, morpholinium, 3-pyridylammonium, piperidinium or piperazinium, or ammonium which is derived from an amino acid or its esters, such as $NH_3$—$CH_2$—$COOCH_3$.

Accordingly, phosphonium containing organic substituents, organic sulfonium or organic sulfoxonium contain aliphatic or arylaliphatic radicals.

Examples of other nitrogen cations are hydrazonium, hydroxylammonium, guanidinium, aminoguanidinium and their substitution products.

Preferred compounds of the formula I are those wherein

R denotes a radical of the formulae

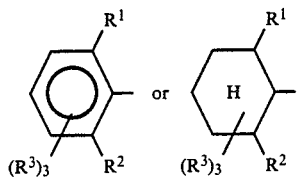

X denotes a radical of the formulae

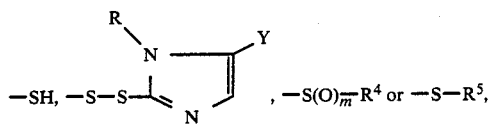

Y denotes a radical of the formulae

m denotes 0, 1 or 2
n denotes 0, 1, 2 or 3,
$R^1$ and $R^2$ independently of one another denote ($C_1$-$C_4$)-alkyl,
the radicals $R^3$ independently of one another denote hydrogen, ($C_1$-$C_4$)-alkyl or halogen,
$R^4$ denotes ($C_1$-$C_4$)-alkyl, ($C_3$ or $C_4$)-alkenyl, propargyl, ($C_1$ or $C_2$)-alkoxycarbonyl-($C_1$ or $C_2$)-alkyl, phenyl or benzyl,
$R^5$ denotes ($C_1$-$C_4$)-alkylcarbonyl,
$R^6$ denotes hydrogen or ($C_1$-$C_6$)-alkyl which is mono-substituted to trisubstituted by ($C_1$ or $C_2$)-alkoxy, or denotes phenyl, a radical of the formulae —$N$=$C(R^{12})_2$ or

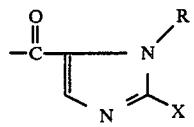

or a cation which can be used for agriculture,
the radicals $R^8$ in each case independently of one another denote hydrogen, ($C_1$-$C_6$)-alkyl, phenyl, benzyl or methylphenyl,
$R^9$ denotes hydrogen or ($C_1$-$C_6$)-alkyl or a radical of the formulae —$OR^8$, —$NH$—$CO$—$NH_2$ or —$NH$—$CS$—$NH_2$,
the radicals $R^{12}$ independently of one another denote ($C_1$ or $C_2$)-alkyl,
and their salts and quaternization products which are acceptable for agricultural purposes.

Particularly preferred compounds of the formula I are those in which

R denotes

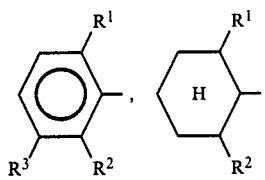

X denotes
Y denotes

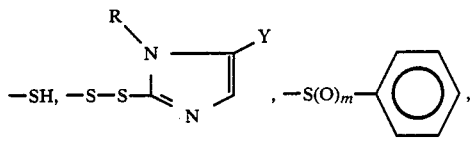

m denotes 0, 1 or 2,
$R^3$ denotes H or halogen,
$R^6$ denotes H, ($C_1$-$C_6$)-alkyl or —$N$=$C(CH_3)_2$ or a cation,
$R^8$ and $R^9$ denote H or ($C_1$-$C_6$)-alkyl.

The invention furthermore relates to processes for the preparation of the compounds of the general formula (I), wherein (a) a bisformyl ester of the formulae IIa or IIb

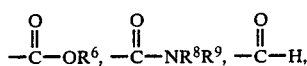

wherein
$R^6$ denotes ($C_1$-$C_{12}$)-alkyl,
($a_1$) is cyclized with a ($C_1$-$C_3$)-carboxamide or
($a_2$) is reacted with an alkali metal thiocyanate or ammonium thiocyanate to give a 2-mercaptoimidazole of the formula I (X=SH, Y=—$COOR^6$), or
(b) an imidazole compound of the formula III

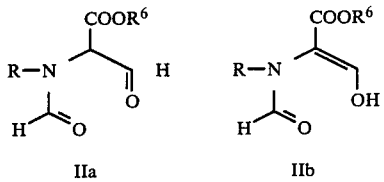

is metallized with a strong base in the 2-position of the imidazole ring and then reacted with a disulfide of the formula $R^4$—S—S—$R^4$ to give a compound of the formula I in which X=—S—$R^4$ and Y=-$COO(C_1$-$C_{12})$-alkyl,
and the compounds obtained under (a) or (b) are, if required, derivatized.

To effect derivatization, the radical —$COOR^6$ or —$COO(C_1$-$C_{12})$-alkyl is converted in a known manner to other radicals stated for Y, for example by hydrolysis, esterification, transesterification, amidation, salt formation, reduction, oximation, etc., as described in, for example, German Offenlegungsschriften Nos. 3,444,918 and 3,442,690, or salt formation or quaternization is carried out in a conventional manner at the basic nitrogen atom of the imidazole ring.

The derivatization of the radical X, starting from the —SH compound of the formula I obtained according to variant (a), is carried out by conventional methods, such as, for example, alkylation, acylation, carbamoylation, salt formation or oxidation.

Conversion to the compounds of the formula I in which $X=-SR^5$ is effected by reaction with a suitable anhydride, acyl chloride or isocynate (Houben-Weyl, Methoden der organischen Chemie (Methods of Organic Chemistry), Volume IX, page 745 et seq.), or with a base capable of salt formation.

The oxidation of compounds of the formula I in which X=SH initially gives disulfides in which

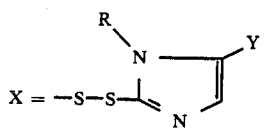

(Houben-Weyl, Volume IX, page 59 et seq.), whcih can be converted to the compounds of the formula I in which $X=-SSR^1$ by reaction with mercaptans of the formula $R^1$—SH in the presence of aCids (Houben-Weyl, Volume IX, page 77 et seq.).

The compounds of the formula I in which $X=S-R^4$, obtained by variant (b), can be converted to the compounds in which $X=-SO-R^4$ or $-SO_2-R^4$ by reaction with one or two equivalents of an oxidizing agent, such as m-chloroperbenzoic acid. Furthermore, where $R^4$ denotes a suitable protective group, for example $R^4$=benzyl, it is also possible to obtain a mercapto compound of the formula I (X=S—H) after elimination of $R^4$, for example with sodium/ethanol or sodium in ammonia, by variant b), and the said mercapto compound can, if required, be further derivatized as described for variant a).

Re (a): In process (a₁), formamide is preferably employed as the carboxamide. It is preferably reacted in the presence of a mineral acid in molar amounts at 50°-200° C., in particular 100°-170° C.

The reaction of the bisformyl ester II a or II b with an alkali metal thiocyanate or ammonium thiocyanate is advantageously carried out in the presence of a solvent, such as an ether, for example tetrahydrofuran or dioxane, or a halogenated hydrocarbon and molar amounts of inorganic acids—to liberate the hydrogen thiocyanate—such as, for example, hydrochloric acid, at temperatures of 0° C. to the boiling point of the solvent, advantageously betweeen 20° and 60° C. When the reaction is complete, the product is isolated by extraction and, if required, purified by chromatography.

Re (b): Suitable bases for the metallization are sodium amide, alkyllithium compounds or lithium amides, such as, for example, lithium diisopropylamide or lithium cyclohexylisopropylamide, in inert solvents, such as tetrahydrofuran, hexamethylphosphoric acid triamide or 1,3-dimethylimidazolin-2-one. The temperatures during metallization are usually −50° to −78° C. After the addition of the disulfide, the mixture is allowed to warm up to room temperature, hydrolysis is carried out with ammonium chloride, and the product is isolated by extraction. The alkyl-thio compounds are obtained in this process in very good yield and purity.

The bisformyl compounds of the formula IIa or IIb can readily be prepared by known methods (German Offenlegungsschrift No. 3,217,094 or R. G. Jones, J. Am. Chem. Soc., 71, (1949), 644) from the corresponding anilines or amines.

The phenylimidazole compounds III are likewise known from the literature (see German Offenlegungsschrift No. 3,217,094, German Offenlegungsschrift No. 3,444,918 and German Offenlegungsschrift No. 3,514,116).

With the compounds accordin to the invention, it is possible to achieve typical growth-regulating effects which—compared with the compounds known from DE-A No. 32 17 094—are observed in various crops even at low doses. The compounds of the formula I have a regulating effect on the plant's metabolism and can therefore be employed for selectively influencing plant ingredients and for facilitating harvesting, and also for initiating desiccation and growth inhibition. They are also suitable for generally controlling and inhibiting undesired vegetative growth without killing the plants in the process. Inhibition of vegetative growth plays an important role in many monocotyledon and dicotyledon crops since it can reduce or completely prevent lodging. Particularly noteworthy is the growth-regulating activity of the compounds as growth inhibitors in cereals, corn, soybean, tobacco, cotton, field beans, rape, rice and lawns, and their ability to increase the content of desired ingredients, such as carbohydrates (for example sugar cane or millet crops) and protein in useful plants. Finally, the compounds produce a very great improvement in fruit abscission, in particular in the case of citrus fruit.

The application furtheremore relates to plant growth-regulating agents which are distinguished by an effective content of at least one compound of the general formula (I). The application rate for the compound according to the invention is in general 0.02 to 1.5 kg of active substance per ha, preferably 0.05 to 1 kg/ha.

When used in practice, the compounds according to the invention can, if appropriate, also advantageously be combined with known growth regulators. Such known growth regulators are the compounds of the formula

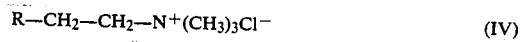

wherein

R denotes OH or Cl (common name chlormequat for R=Cl), and N,N-dimethylpiperidinium chloride (V, mepiquate chloride), α-cyclopropyl-4-methoxy-α-(pyrimidin-5-yl)benzyl alcohol (VI, ancymidol), (3aα, 4β, 4aα, 6aα, 7β, 7aα)-1-(4-chlorophenyl)-3a, 4, 4a, 6a, 7, 7a-hexahydro-4,7-methano-1H-[1,2]diazeto[3,4-f]benzotriazole (VII, tetcylacis), succinic acid mono-2,2-dimethylhydrazide (VIII, diaminoazide), 6-hydroxy-2H-pyriazin-3-one (IX, maleic hydrazide), 2-chloro-9-hydroxy-9H-fluorene-9-carboxylic acid (X, chloroflurenol), 5'-(trifluoromethanesulfonamido)acet-2',4'-xylidide (XI, mefluidide) and 2-chloroethylphosphonic acid (XII, ethephon).

The growth-regulating actions of the compounds of the formulae (IV) to (XII) are described in Plant Growth Regulator Handbook of the Plant Growth Regulator Working Group, 2nd ed. (1981).

Instead of the compounds of the formulae (VI) and (V), it is also possible in principle to use comparable salts which, instead of the chloride ion, contain another customary anion, such as bromide, nitrate or ½ sulfate.

Surprisingly, when the compounds of the formula (I) were combined with the compounds of the formula (IV) to (XII), striking synergistic effects were exhibited.

Thus, these combinations can be employed in even lower doses than would be expected from the action of the individual components, in order to achieve the desired effects. When the combinations, it is also possible to reduce the occurrence of natural vegetation, so that the combinations can also be employed in landscape care. The combinations are also outstandingly suitable for generally controlling and inhibiting undesired vegetative growth, such as the production of side shoots, without killing the plants. The compounds of the formula (I) can also advantageously be combined with two different compounds of the formulae (IV) to (XII).

The mixing ratios of the components of the general formula (I) with the compounds of the formulae (IV) to (XII) an vary within the wide limits, approximately between 250:1 and 1:10. The choice of the mixing ratio is independent of the type of components in the mixture, of the stage of development of the plants and of the degree of the desired growth-regulating action. Mixing ratios of 10:1 to 1:10 are preferably chosen.

The application rate for the compounds of the formula (I) in the mixtures of active substances is in general between 0.05 and 1 kg of active substance per ha, and the application rates for the compounds of the formula (IV) to (XII) vary between 0.01 and 5 kg of active substance/ha. The combinations either may occur as mixed formulations of the components, which are then used in a customary manner diluted with water, or may be prepared as so-called tank mixes by diluting the separately formulated components together with water; it is also possible to use the components one after the other, i.e. the components are then applied in individual formulations.

The compounds of the general formula (I) can also be combined with natural or vegetable hormones, such as auxins or cytokins.

The compounds according to the invention, of the general formula (I), is appropriate as a mixture with further active components, such as the compounds of the formulae II to XII, can be used in the customary formulations as wettable powders, emulsifiable concentrates, atomizable solutions, dusting agents, dressings, dispersions, granules or microgranules.

Wettable powders are preparations which can be dispersed homogeneously in water and which, in addition to the active substance or substances and, if appropriate, a diluent or inert substance, also contain wetting agents, such as polyoxyethylated fatty alcohols, alkyl sulfonates or alkylphenyl sulfonates, and/or dispersants, such as sodium lignin sulfonate, sodium 2,2'-dinaphthylmethane-6,6'-disulfonate, sodium dibutylnaphthalene sulfonate or sodium oleoylmethyltaurate. The preparation is carried out in a customary manner, for example by milling and mixing the components.

Emulsifiable concentrates can be prepared, for example, by dissolving the active substance or substances in an inert organic solvent, such as butanol, cyclohexanone, dimethylformamide, xylene or relatively high boiling aromatics or aliphatic or cycloaliphatic hydrocarbons, with the addition of one or more emulsifiers. In the case of liquid active substances, some or all of the solvent may be dispensed with. Examples of emulsifiers which can be used are: calcium alkylarylsulfonates, such as Ca dodecylbenzenesulfonate, and nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide condensation products, alkyl polyglycol ethers, sorbitan fatty acid esters, polyoxoethylene sorbitan fatty acid esters and polyoxoethylene sorbitol esters.

Dusting agents can be obtained by milling the active substance or substances with finely divided, solid substances, for example talc or natural clays, such as kaolin, bentonite, pyrophillite or diatomaceous earth. Granules can be prepared either by atomizing the active substance or substances onto adsorptive, granulated inert material or by applying active substance concentrates by means of binders, for example polyvinyl alcohol, sodium polyacrylate or mineral oils, onto the surface of carriers, such as sand, kaolinite or granulated inert material. It is also possible for suitable active substances to be granulated in the manner customary for the preparation of fertilizer granules—if desired as a mixture with fertilizers.

In wettable powders, the concentration of active substance is about 10 to 90% by weight, the remainder to 100% by weight consisting of customary formulation components. In the case of emulsifiable concentrates, the concentration of active substance can be about 5 to 80% by weight. Dust-like formulations generally contain 0.025 to 20% by weight of active substance or substances, while atomizable solutions contain about 2 to 20% by weight. In the case of granules, the content of active substance depends in part on whether the active compound is liquid or solid and what granulation auxiliaries, fillers, etc are used. Furtheremore, the stated formulations of active substances contain the adhesives, wetting agents, dispersants, emulsifiers, penetration agents, solvents, fillers or carriers which are customary in each case.

For use, the concentrates present in commercial form are, if required, diluted in a customary manner, for example in the case of wettable powders, emulsifiable concentrates, dispersions and in some cases microgranules by means of water. Dust-like and granulated formulations and atomizable solutions are not usually further diluted with other inert substances before being used.

Mixtures or mixed formulations with other active substances, such as insecticides, acaracides, herbicides, fertilizers or fungicides, may also be possible.

FORMULATION EXAMPLES

EXAMPLE 1

A dusting agent was obtained by (a) mixing 10 parts by weight of active substance or substances and 90 parts by weight of talc or another inert substance and comminuting the mixture in an impact mill, or by (b) homogenizing 60 parts by weight of active substance, 35 parts by weight of talc and 5 parts by weight of an adhesive (for example a polysaccharide, such as ®Rhodopol from Rhône-Poulenc S.A.) in the same manner.

EXAMPLE 2

A wettable powder readily dispersible in water was obtained by mixing 25 parts by weight of active substance or substances, 64 parts by weight of kaolin-containing quartz as an inert substance, 10 parts by weight of potassium ligninsulfonate and 1 parts by weight of sodium oleoylmethyltaurate as a wetting agent and a dispersant, and milling the mixture in a pinned-disk mill. A formulation containing 5% of active substance may have the following composition: 5% of active substance or substances, 6% of a sulfonated naphthalene/formaldehyde condensate (for example ®Dispersogen A from Hoechst AG), 2% of a Na salt of an alkyl naphthalene sulfonic acid (for example ®Leonil DB from Hoechst AG), 5% of a mixture of polypropylene glycol and SiO$_2$ (for example ®Acrotin 341 from Hoechst AG), 25% of an SiO$_2$ (for example ®Sipernat from Degussa AG) and 57% of kaolin type 1777.

EXAMPLE 3

A dispersion concentrate which is readily dispersible in water was obtained by mixing 20 parts by weight of active substance or substances with 6 parts by weight of an alkylphenol polyglycol ether (for example ®Triton X 207 from Rohm and Haas Co.), 3 parts by weight of isotridecanol polyglycol ether (8 ethylene oxide units) and 71 parts by weight of paraffinic mineral oil (boiling range from about 255° to above 377° C.) and milling the mixture in a ball mill to a fineness of less than 5 μm.

EXAMPLE 4

An emulsifiable concentrate was obtained from 15 parts by weight of active substance or substances, 75 parts by weight of cyclohexanone as solvent and 10 parts by weight of oxyethylated nonylphenol (10 ethylene oxide units) as emulsifier.

CHEMICAL EXAMPLES

EXAMPLE 1

Methyl 1-(2,6-dimethylcyclohexyl)-2-mercaptoimidazole-5-carboxylate

A solution of 19.4 g (0.20 mol) of potassium thiocyanate in 100 ml of water was added to 29.7 g (0.10 mol) of methyl 2-(N-formyl-2,6-dimethylcyclohexylamino)-3-hydroxyacrylate in 200 ml of tetrahydrofuran. After the dropwise addition of 22 g of concentrated hydrochloric acid, the mixture was heated for 12 hours at 60° C. After the mixture had cooled, the organic phase was separated off and evaporated down. After chromatographic purification, 21.3 g (76% of theory) of methyl 1-(2,6-dimethylcyclohexyl)-2-mercaptoimidazole-5-carboxylate were obtained as yellow oil.

EXAMPLE 2

Ethyl 2-benzylthio-1-(2,6-diethylphenyl)-imidazole-5-carboxylate 27.2 g (0.10 mol) of ethyl 1-(2,6-diethylphenyl)-imidazole-5-carboxylate were added dropwise, in the course of 1 hour at −70° to −78° C., to a solution of 12.2 g (0.12 mol) of diisopropylamine and 80 ml (0.13 mol) of 15% strength butyllithium solution in hexane in 100 ml of absolute tetrahydrofuran. Stirring was continued for 10 minutes, and a solution of 32.0 g (0.13 mol) of dibenzyl disulfide in 50 ml of tetrahydrofuran was then added dropwise. The mixture was allowed to warm up to room temperature, 10 ml of saturated ammonium chloride solution were added dropwise, and the reaction mixture was poured onto 500 ml of water and extracted twice with toluene. After evaporation and chromatography (silica gel, mobile phase 8:2 petroleum ether (low)/ethyl acetate), 33.5 g (85% of theory) of ethyl 2-benzylthio-1-(2,6-diethylphenyl)-imidazole-5-carboxylate were obtained as a colorless oil.

$^1$H-NMR (CDCl$_3$, 60 MHz)=0.9–1.3 (m, 9H, CH$_3$); 2.15 (q, J=7 Hz, phenyl-CH$_2$, 4H); 4.01 (q, J=7 Hz, O—CH$_2$, 2H); 4.40 (s, 2H, —S—CH$_2$); 7.1–7.4 (m, 8H, phenyl-H), 7.87 (s, 1H, imidazole-H)ppm.

EXAMPLE 3

Ethyl 2-benzylsulfinyl-1-(2,6-diethylphenyl)-imidazole-5-carboxylate 5.7 g (0.028 mol) of m-chloroperbenzoic acid were added to 10 g (0.025 mol) of ethyl 2-benzylthio-1-(2,6-diethylphenyl)-imidazole-3-carboxylate in 50 ml of chloroform at room temperature. After 1 hour, the m-chloroperbenzoic acid which is separated off was filterd off under suction, and the mother liquor was washed twice with bicarbonate solution, dried over sodium sulfate and evaporated down. Ethyl 2-benzylsulfinyl-1-(2,6-diethylphenyl)-imidazole-5-carboxylate was obtained in quantitative yield; colorless solid of melting point 82°–83° C.

EXAMPLE 4

Ethyl 2-benzylsulfonyl-1-(2,6-diethylphenyl)-imidazole-5-carboxylate

The sulfonyl compound was obtained in quantitative yield analogously to Example 3 but using twice the molar amount of m-chloroperbenzoic acid; colorless solid of melting point 62°–66° C.

EXAMPLE 5

2-benzylthio-1-(2,6-diethylphenyl)-imidazole-5-carboxylic acid 31.5 g (0.08 mol) of ethyl 2-benzylthio-1-(2,6-diethylphenyl)-imidazole-5-carboxylate (cf. Example 2) were stirred with 30 g of 33% strength sodium hydroxide solution at 80° C. until a homogeneous solution was formed. The solution was allowed to cool and acidified to pH 3 with dilute hydrochloric acid, and the product was filtered off under suction and dried in vacuo. 26.4 g (90% of theory) of 2-benzylthio-1-(2,6-diethylphenyl)-imidazole-5-carboxylic acid, solid at melting point 152°–154° C., were obtained.

EXAMPLE 7

1-(2,6-diethylphenyl)-2-mercaptoimidazole-5-carboxylic acid 2.3 g (0.1 mol) of sodium were added in portions to a suspension of 5 g (0.014 mol) of 2-benzylthio-1-(2,6-diethylphenyl)-imidazole-5-carboxylic acid in 50 ml of liquid ammonia at −40° to −50° C. After 1 hour, 6 g of ammonium chloride were added at the same temperature, and the mixture was allowed to warm up to room temperature overnight. The residue was taken up in 200 ml of water, and the solution was acidified to pH 3 with semiconcentrated hydrochloric acid and filtered under suction. 3.0 g (79% of theory) of 1-(2,6-diethylphenyl)-2-mercaptoimidazole-5-carboxylic acid, a solid having a melting point above 230° C., were obtained.

EXAMPLE 7 (SALT FORMATION)

Piperidinium 2-benzylsulfonyl-1-(2,6-diethylphenyl)-imidazole-5-carboxylate 6.5 g (0.016 mol) of 2-benzylsulfonyl-1-(2,6-diethylphenyl)-imidazole-5-carboxylic acid were stirred with 1.6 g (0.019 mol) of piperidine in 50 ml of methylene chloride until the carboxylic acid had dissolved. The solution was evaporated down, the residue was brought to crystallization with ether, and the solid was filtered off under suction and dried to give 6.9 g (87% of theory) of piperidinium 2-benzylsulfonyl-1-(2,6-diethylphenyl)-imidazole-5-carboxylate, a colorless solid of melting point 167°–170° C.

Other examples are listed in Table 1

TABLE 1

Imidazole compounds of the formula I

| Example No. | R | X | Y | Mp [°C.] |
|---|---|---|---|---|
| 8 | 2,6-Dimethylphenyl | —SH | COOH | Resin |
| 9 | " | " | COO$^\ominus$.N$^\oplus$(—C$_2$H$_5$)$_4$ | " |
| 10 | " | —S—C$_4$H$_9$ | COO—i-C$_3$H$_7$ | Oil |
| 11 | " | " | CONHNHCHO | " |
| 12 | " | —S—S—C$_2$H$_5$ | COOH | " |
| 13 | " | —S—COCH$_3$ | CONH—NH—CO—Phenyl | " |
| 14 | " | " | COOH.NH$_3$ | Foam |
| 15 | " | —S—COC(CH$_3$)$_3$ | CONH—NH$_2$ | Oil |
| 16 | 2-Ethyl-6-methylphenyl | —SH | COOH | " |
| 17 | " | " | COOCH$_3$ | " |
| 18 | " | —SNa | COONa | Resin |
| 19 | " | —SH | COONa | " |
| 20 | " | " | COOH.H$_2$NCH$_3$ | Oil |
| 21 | " | " | COO—N=C(CH$_3$)$_2$ | " |
| 22 | " | " | CONHCH$_3$ | " |
| 23 | " | " | CON(CH$_3$)Phenyl | " |
| 24 | " | " | COOCH$_2$—COOCH$_3$ | " |
| 25 | " | " | COOLi | " |
| 26 | " | " | COO.½Mg | Resin |
| 27 | 2-Ethyl-6-methylphenyl | —SH | CONHOH | Oil |
| 28 | " | —S—Phenyl | COOH | " |
| 29 | " | —S—Benzyl | COOH | " |
| 30 | " | —S—CH$_2$—CH=CH$_2$ | COOH | " |
| 31 | " | —S—CH$_2$—CH=CH$_2$ | COO—n-C$_8$H$_{17}$ | " |
| 32 | " | —S—CH$_2$—COOCH$_3$ | COOC$_2$H$_5$ | " |
| 33 | " | —S—CH(CH$_3$)—COO$_2$H$_5$ | COO—C$_6$H$_{11}$ | " |
| 34 | " | —S—CH$_3$ | COO—(2-methylcyclohexyl) | " |
| 35 | " | —S—CH$_3$ | (isoxazoline-dimethyl group) | " |
| 36 | 2,6-Diethylphenyl | —SH | COOH.HN-piperidinyl | 194–5 |
| 37 | " | —SH | COOH.N(CH$_2$—CH$_2$—OH)$_3$ | 140–3 |
| 38 | " | —SH | COONa | Foam |
| 39 | " | —SH | COOK | Resin |
| 40 | " | —SH | COOH.HN(CH$_3$)$_2$ | Oil |
| 41 | " | —SH | COOH.N(CH$_3$)$_3$ | " |
| 42 | " | —SH | COOH.H$_2$N—CH$_2$—CH$_2$—CH$_2$—OCH$_3$ | Oil |
| 43[1] | " | —SH | COOH | Resin |
| 44[2] | " | —SH | COOH | " |
| 45 | " | —S—CH$_3$ | COOH | 197–200 |
| 46 | " | —S—CH$_3$ | COOC$_2$H$_5$ | Oil |
| 47 | " | —SOCH$_3$ | COOC$_2$H$_5$ | Oil |
| 48 | " | —SO$_2$CH$_3$ | COOC$_2$H$_5$ | 119–121 |
| 49 | " | —S—CH$_2$—Phenyl | COOH.N(CH$_2$—CH$_2$—OH)$_3$ | 80–6 |
| 50 | " | —SOCH$_2$—Phenyl | CONHOH | Oil |

TABLE 1-continued

Imidazole compounds of the formula I $$\begin{array}{c} R-N \diagdown \diagup Y \\ \phantom{xxx} \\ X \diagup \diagdown N \end{array}$$

| Example No. | R | X | Y | Mp [°C.] |
|---|---|---|---|---|
| 51 | " | —SO₂—CH₂—Phenyl | COOH | 168–171 |
| 52 | 2,6-Diethylphenyl | —SO₂—CH₂—Phenyl | COOH.N⁺(CH₂—CH₂—OH)₃ | 116–18 |
| 53 | " | —S—S— (imidazole ring with R, COOH) | COOH | Resin |
| 54 | " | —S—S— (imidazole ring with R, COOCH₃) | COOCH₃ | Oil |
| 55 | " | —SH | —C(CH₃)=N—O— (isoxazoline ring) | " |
| 56 | 2,6-Diethyl-3-methylphenyl | —S—H | COOH | " |
| 57 | " | —S—CH₂—Phenyl | COOCH₂—COOCH₃ | " |
| 58 | 2,6-Diethyl-4-methylphenyl | —SH | —COOH | " |
| 59 | " | —S—COOC₂H₅ | —COOCH₂—CH₂—O—CH₃ | " |
| 60 | " | —S—CO—Phenyl | —CONH—N(CH₃)₂ | " |
| 61 | " | —S—CO—NHCH₃ | —CONH₂ | " |
| 62 | 4-Bromo-2,6-diethylphenyl | —SH | —COOH | Resin |
| 63 | " | —SH | —COOCH₂—4-chlorophenyl | Oil |
| 64 | " | —SH | —COOH.HN(morpholine) | Oil |
| 65 | 2-Ethyl-6-isopropylphenyl | SH | —COOH | Resin |
| 66 | " | S—COCOOCH₃ | —COOH | Oil |
| 67 | " | SH | —CON(2,6-dimethylmorpholine) | " |
| 68 | 2-tert.-Butyl-6-methylphenyl | SH | —COOH | Resin |
| 69 | " | SH | —COCH₃ | Oil |
| 70 | " | SH | —C(CH₃)=N—OH | " |
| 71 | " | SH | —C(NH₂)=N—OH | " |
| 72 | " | SH | —CN | " |
| 73 | 2-Ethyl-6-methylcyclohexyl | SH | —COOH | " |
| 74 | " | SH | —CHO | " |
| 75 | " | SH | —CH₂OH | " |
| 76 | " | SH | —CHNOH | " |
| 77 | " | SH | —CHNOCH₃ | " |
| 78 | 2,6-Diethylcyclohexyl | SH | —COOH | Resin |
| 79 | " | SH | —COOCH₃ | Oil |
| 80 | " | SH | —COOC₂H₅ | " |
| 81 | " | SH | —CONH₂ | " |
| 82 | " | SH | —CONH—Phenyl | " |
| 83 | " | SH | —COO⁻.N⁺(CH₂—CH₂—Cl)(CH₃)₃ | " |
| 84 | 2,6-Diethylcyclohexyl | —S—CH₃ | —COOC₂H₅ | Oil |
| 85 | " | —SOCH₃ | —COOC₂H₅ | Oil |
| 86 | 2,6-Diethylcyclohexyl | —SO₂—CH₃ | —COOC₂H₅ | Oil |

TABLE 1-continued

Imidazole compounds of the formula I

| Example No. | R | X | Y | Mp [°C.] |
|---|---|---|---|---|
| 87 | " | —S—CH$_2$—Phenyl | —COOC$_2$H$_5$ | Oil |
| 88 | " | " | —COOH | 116-24 |
| 89 | " | —S—S—[imidazole with N-R, COOH] | —COOH | Oil |
| 90 | " | —S—CH$_3$ | —COO—C(=O)—[imidazole with R, S—CH$_3$] (vinyl linkage) | " |
| 91[3] | " | —SH | —COOH | Resin |
| 92 | " | —S$^⊕$—(CH$_3$)$_3$I$^⊖$ | —COOC$_2$H$_5$ | Oil |
| 93 | " | —S—CH$_3$ | —COO—CH$_2$—COOH | " |
| 94 | " | " | —C[tetrazole N—N, N—N—H] | " |
| 95 | " | " | —CH(SC$_2$H$_5$)$_2$ | " |
| 96 | " | " | —C(=S)—NH$_2$ | " |
| 97 | " | " | [imidazoline N, N—H ring] | " |
| 98 | 2,6-Diethylphenyl | —S—Phenyl | COOH | 212-4 |
| 99 | " | " | COOC$_2$H$_5$ | Oil |
| 100 | " | —S(O)—Phenyl | " | " |
| 101 | " | —S(O)$_2$—Phenyl | " | " |
| 102 | 2,2-Dimethylcyclohexyl | —SH | COOH | Resin |
| 103 | " | " | COOC$_2$H$_5$ | 119-125 |
| 104 | 2-Ethyl-6-methylcyclohexyl | —SCH$_3$ | COOC$_2$H$_5$ | Oil |
| 105 | 2,6-Diethylcyclohexyl | —S—C(=O)CH$_3$ | COOC$_2$H$_5$ | " |
| 106 | " | —S—CH$_2$—Phenyl | COOC$_2$H$_5$ | " |
| 107 | 2,6-Diethylcyclohexyl | " | COOH·HN[piperidine] | 109-112 |
| 108 | " | —SC$_2$H$_5$ | COOC$_2$H$_5$ | Oil |
| 109 | " | —S—CH(CH$_3$)$_2$ | " | Oil |
| 110 | " | —S—CH$_2$—CH=CH$_2$ | " | " |
| 111 | " | —S—CH$_2$—C≡CH | " | " |
| 112 | " | —S—CH$_2$—COOC$_2$H$_5$ | " | " |
| 113 | " | —S—CH$_2$—COOH | COOH | Resin |
| 114 | " | —S—S—[oxazole with COOC$_2$H$_5$, N—R] | COOC$_2$H$_5$ | Oil |

TABLE 1-continued

Imidazole compounds of the formula I

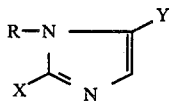

| Example No. | R | X | Y | Mp [°C.] |
|---|---|---|---|---|
| 115 | 3-Chlor-2,6-diethylphenyl | —SH | COOH | Resin |
| 116 | " | " | COOC$_2$H$_5$ | Oil |
| 117 | " | " | C(=O)NH$_2$ | " |

[1]Hydrochloride
[2]Sulfate
[3]Chloroethylphosphonate

BIOLOGICAL EXAMPLES

1. Growth Inhibition in Cereals

In tests carried out in vessels in a greenhouse, young cereal plants (wheat, barley, rye) in the 3-leaf stage were sprayed, until dripping wet, with compounds according to the invention, using different concentrations of active substance (kg/ha).

After the untreated control plants had reached a height of about 55 cm, the additional growth of all plants was measured, and the inhibition of growth was calculated as a percentage of the additional growth of the control plants. The phytotoxic effect of the compound was also observed. The inhibition of growth was determined as a percentage value, 100% denoting no growth and 0% denoting growth corresponding to that of the untreated control plants. It was found that the compounds possess very good growth-regulating properties (see Table 2).

2. Inhibition of Growth in Paddy Rice

Rice plants were grown, and treated with compounds according to the invention at the stage corresponding to maximum tillering. The substances were both applied by spraying and introduced into the water.

3 weeks after treatment, the additional growth was measured for all plants, and the inhibition of growth was calculated as a % of the additional growth of the control plants. Any phytotoxic effect of the compounds was also observed.

The inhibition of growth was determined as a percentage value, 100% denoting no growth and 0% denoting growth corresponding to that of the untreated control plants. It was found that the compounds possess very good growth-regulating properties (see Table 3).

3. Inhibition of Growth in Soybeans

Soybeans about 10 cm in height were sprayed, until dripping wet, with the formulations of active substances. Rating was carried out after 3 weeks.

The inhibition of growth was determined as a percentage value, 100% denoting no growth and 0% denoting growth corresponding to that of the untreated control plants. It was found that the compounds possess very good growth-regulating properties (see Table 4).

TABLE 2

| Compound according to example No. | Concentration used (kg/ha) | Inhibition of growth in % for | | | Phytotoxic effect |
|---|---|---|---|---|---|
| | | Wheat | Barley | Rye | |
| 5 | 2.5 | 12 | 15 | 11 | No damage |
| | 1.25 | 8 | 9 | 2 | ↓ |
| 6 | 2.5 | 21 | 35 | 15 | ↓ |
| | 1.25 | 15 | 20 | 12 | ↓ |
| 36 | 2.5 | 22 | 36 | 14 | ↓ |
| | 1.25 | 15 | 19 | 12 | ↓ |
| 37 | 2.5 | 22 | 35 | 14 | ↓ |
| | 1.25 | 14 | 20 | 11 | ↓ |
| 45 | 2.5 | 13 | 14 | 10 | ↓ |
| | 1.25 | 9 | 7 | 8 | ↓ |
| 78 | 2.5 | 12 | 14 | 11 | ↓ |
| | 1.25 | 7 | 8 | 6 | ↓ |
| 80 | 2.5 | 11 | 15 | 12 | ↓ |
| | 1.25 | 9 | 8 | 7 | ↓ |
| 99 | 2.5 | 20 | 25 | 21 | ↓ |
| | 1.25 | 14 | 19 | 17 | ↓ |
| 114 | 2.5 | 21 | 23 | 20 | ↓ |
| | 1.25 | 17 | 18 | 16 | ↓ |
| A | 2.5 | 27 | 8 | 10 | |
| | 1.25 | 23 | 0 | 0 | |

A = 2-chloroethyltrimethylammonium chloride

TABLE 3

| Compound according to example No. | Concentration used (kg/ha) | Inhibition of growth (%) | Phytotoxic effect |
|---|---|---|---|
| 5 | 2.5 | 14 | No damage |
| | 1.25 | 9 | ↓ |
| 6 | 2.5 | 17 | ↓ |
| | 1.25 | 12 | ↓ |
| 36 | 2.5 | 18 | ↓ |
| | 1.25 | 11 | ↓ |
| 37 | 2.5 | 23 | ↓ |
| | 1.25 | 19 | ↓ |
| 45 | 2.5 | 15 | ↓ |
| | 1.25 | 7 | ↓ |
| 78 | 2.5 | 14 | ↓ |
| | 1.25 | 11 | ↓ |
| 80 | 2.5 | 13 | ↓ |
| | 1.25 | 10 | ↓ |
| 99 | 2.5 | 7 | ↓ |
| | 1.25 | 6 | ↓ |
| 114 | 2.5 | 19 | ↓ |
| | 1.25 | 17 | ↓ |

TABLE 4

| Compound according to example No. | Concentration used (kg/ha) | Inhibition of growth (%) | Phytotoxic effect |
|---|---|---|---|
| 5 | 2.5 | 14 | No damage |
| 6 | 2.5 | 21 | ↓ |

TABLE 4-continued

| Compound according to example No. | Concentration used (kg/ha) | Inhibition of growth (%) | Phytotoxic effect |
| --- | --- | --- | --- |
| 36 | 2.5 | 24 | ↓ |
| 37 | 2.5 | 22 | ↓ |
| 45 | 2.5 | 11 | ↓ |
| 78 | 2.5 | 9 | ↓ |
| 80 | 2.5 | 11 | ↓ |
| 99 | 2.5 | 16 | ↓ |
| 114 | 2.5 | 17 | ↓ |

What is claimed is:

1. A compound of the formula I

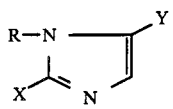
I wherein
R denotes a radical of the formulae

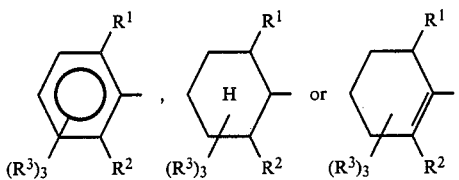

X denotes a radical of the formula —SH,
Y denotes a radical of the formula

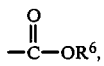

$R^1$ and $R^2$ independently of one another denote $(C_1-C_4)$-alkyl, and
the radicals $R^3$ independently of one another denote hydrogen, $(C_1-C_4)$-alkyl, $(C_1-C_4)$-alkoxy, or halogen, or a salt or a quaternization product thereof which is acceptable for agricultural purposes.

2. A compound of the formula I as claimed in claim 1, wherein
R denotes a radical of the formulae

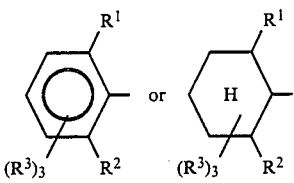

X denotes a radical of the formula —SH,
Y denotes a radical of the formula

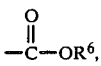

$R^1$ and $R^2$ independently of one another denote $(C_1-C_4)$-alkyl,
the radicals $R^3$ independently of one another denote hydrogen, $(C_1-C_4)$-alkyl or halogen,
$R^6$ denotes hydrogen or $(C_1-C_6)$-alkyl,
or a salt or a quaternization product thereof which is acceptable for agricultural purposes.

3. A plant growth-regulating agent containing an effective amount of a compound of the formula (I) of claim 1 and a suitable carrier.

4. A method for regulating plant growth, wherein an effective amount of a compound of the formula (I) of claim 1 is applied to the plants or the cultivated area.

5. The compound Methyl 1-(2,6-dimethyl-cyclohexyl)-2-mercaptoimidazole-5-carboxylate.

6. The compound 1-(2,6-diethylphenyl)-2-mercaptoimidazole-5-carboxylic acid or a salt thereof.

7. The compound Ethyl 1-(2,6-diethyl-cyclohexyl)-2-mercaptoimidazole-5-carboxylate.

8. The compound as claimed in claim 1 which is 1-(2,6-diethylcyclohexyl)-2-mercapto-imidazol-5-carboxylic acid.

* * * * *